(12) United States Patent
Petit

(10) Patent No.: US 10,751,739 B2
(45) Date of Patent: Aug. 25, 2020

(54) DEVICE FOR DISPENSING A FLUID PRODUCT

(71) Applicant: APTAR FRANCE SAS, Le Neubourg (FR)

(72) Inventor: Ludovic Petit, Vitot (FR)

(73) Assignee: APTAR FRANCE SAS, Le Neubourg (FR)

( * ) Notice: Subject to any disclaimer, the term of this patent is extended or adjusted under 35 U.S.C. 154(b) by 0 days.

(21) Appl. No.: 16/098,199

(22) PCT Filed: May 2, 2017

(86) PCT No.: PCT/FR2017/051036
§ 371 (c)(1),
(2) Date: Nov. 1, 2018

(87) PCT Pub. No.: WO2017/191400
PCT Pub. Date: Nov. 9, 2017

(65) Prior Publication Data
US 2019/0176175 A1 Jun. 13, 2019

(30) Foreign Application Priority Data
May 4, 2016 (FR) ..................................... 16 54057

(51) Int. Cl.
*B05B 11/00* (2006.01)
*B05B 11/02* (2006.01)
(Continued)

(52) U.S. Cl.
CPC ....... *B05B 11/0027* (2013.01); *A61M 11/007* (2014.02); *A61M 15/004* (2014.02);
(Continued)

(58) Field of Classification Search
CPC .. B05B 11/0027; B05B 11/02; A61M 15/004; A61M 15/0028; A61M 15/0036;
(Continued)

(56) References Cited

U.S. PATENT DOCUMENTS 5,289,818 A * 3/1994 Citerio ................... B05B 11/02
128/200.14
5,503,302 A * 4/1996 DeJonge ............. B05B 11/0038
222/82
(Continued)

FOREIGN PATENT DOCUMENTS

DE 197 00 437 A1 7/1997
DE 200 22 559 U1 11/2001
(Continued)

OTHER PUBLICATIONS

International Search Report for PCT/FR2017/051036 dated Jul. 5, 2017.
(Continued)

*Primary Examiner* — Lien M Ngo
(74) *Attorney, Agent, or Firm* — Sughrue Mion, PLLC

(57) ABSTRACT

A fluid dispenser device comprising a body (10) that supports, in stationary manner, a reservoir (20) containing fluid, a dispenser head (30) being assembled on said body (10) so as to be axially movable relative to said reservoir (20), said dispenser head (30) being provided with a dispenser orifice (31), said dispenser head (30) including a proximal bearing surface (35) that, during actuation, receives at least one, and typically two, of the user's fingers, and said body (10) including a distal bearing surface (15) that, during actuation, is suitable for receiving one of the user's fingers, and typically the thumb, said device including a removable actuator member (40) that is fastened in removable manner on said body (10) at said distal bearing surface (15), said removable actuator member (40) having a radial dimension (Continued)

that is greater than the radial dimension of said bearing surface (15).

17 Claims, 1 Drawing Sheet

(51) Int. Cl.
*A61M 15/00* (2006.01)
*A61M 11/00* (2006.01)
*A61M 5/31* (2006.01)

(52) U.S. Cl.
CPC .... *A61M 15/0028* (2013.01); *A61M 15/0036* (2014.02); *B05B 11/02* (2013.01); *A61M 5/3137* (2013.01); *A61M 2205/586* (2013.01)

(58) Field of Classification Search
CPC ........ A61M 15/3137; A61M 2205/586; A61M 5/3137
USPC ....... 222/153.13, 82, 326, 329; 604/208–211
See application file for complete search history.

(56) References Cited

U.S. PATENT DOCUMENTS

| | | | |
|---|---|---|---|
| 6,321,942 B1 | 11/2001 | Krampen et al. | |
| 6,364,166 B1 * | 4/2002 | Ritsche | B05B 11/0027 222/153.13 |
| 6,382,465 B1 * | 5/2002 | Greiner-Perth | A61M 15/0065 222/309 |
| 6,708,846 B1 | 3/2004 | Fuchs et al. | |
| 8,734,392 B2 | 5/2014 | Stadelhofer | |
| 8,857,668 B2 * | 10/2014 | Auerbach | B05B 11/0038 222/153.13 |
| 2004/0159679 A1 * | 8/2004 | Greiner-Perth | B05B 11/02 222/153.13 |

FOREIGN PATENT DOCUMENTS

| | | |
|---|---|---|
| EP | 0 546 607 A1 | 6/1993 |
| EP | 1 504 783 A1 | 2/2005 |
| EP | 2 896 421 A1 | 7/2015 |
| FR | 2 970 955 A1 | 8/2012 |
| GB | 2 412 326 A | 9/2005 |
| WO | 99/28042 A1 | 6/1999 |
| WO | 02/102443 A1 | 12/2002 |
| WO | 2010/0139883 A1 | 12/2010 |

OTHER PUBLICATIONS

International Preliminary Report on Patentability with the translation of Written Opinion dated Nov. 15, 2018 issued by the International Bureau in PCT/FR2017/051036.

* cited by examiner

DEVICE FOR DISPENSING A FLUID PRODUCT

CROSS REFERENCE TO RELATED APPLICATIONS

This application is a National Stage of International Application No. PCT/FR2017/051036 filed May 2, 2017, claiming priority based on French Patent Application No. 1654057 filed May 4, 2016.

The present invention relates to a fluid dispenser device, in particular a device of the single-dose or two-dose type, i.e. containing only one or two doses of fluid.

Single-dose or two-dose devices are well known. They generally comprise a reservoir containing one or two doses of fluid, and a dispenser head that is movable relative to said reservoir so as to dispense the fluid, in particular via a piston that slides in said reservoir.

The reservoir may be assembled in a body, with said head assembled on said body. Documents U.S. Pat. No. 8,734,392 and FR 2 970 955 describe devices of this type. In order to avoid accidental or unwanted actuations, blocking means are generally provided, e.g. breakable bridges, that it is necessary to overcome and/or break so as to perform the actuation. Likewise, pre-compression means are also generally provided, so as to ensure that the force that is necessary in order to overcome the pre-compression means provides enough energy to guarantee the complete actuation stroke, and thus so as to ensure that the complete dose is dispensed. Advantageously, the blocking means and the pre-compression means may be formed by the same means, typically breakable bridges.

A drawback with those prior-art devices relates to actuation that might turn out to be difficult, in particular when pre-compression and/or blocking means, such as breakable bridges for example, are provided. This is particularly true when the radial dimensions of the reservoir and/or of the body are small, in particular concerning the area of the bearing surface on which the user presses manually. Another drawback relates to the risk of a malfunction or of an incomplete dose if actuation is not axial.

Documents U.S. Pat. No. 6,708,846, WO 02/102443, EP 0 546 607, EP 1 504 783, DE 200 22 559, EP 2 896 421, WO 99/28042, DE 197 00 437, U.S. Pat. No. 6,321,942, GB 2 412 326, and WO 2010/139883 describe prior-art devices.

An object of the present invention is to provide a device that does not have the above-mentioned drawbacks.

Another object of the present invention is to provide a device that makes actuation easier.

Another object of the present invention is to provide a device that is simple and inexpensive to manufacture and to assemble.

The present thus provides a fluid dispenser device comprising a body that supports, in stationary manner, a reservoir containing fluid, a dispenser head being assembled on said body so as to be axially movable relative to said reservoir, said dispenser head being provided with a dispenser orifice, said dispenser head including a proximal bearing surface that, during actuation, receives at least one, and typically two, of the user's fingers, and said body including a distal bearing surface that, during actuation, is suitable for receiving one of the user's fingers, and typically the thumb, said device including a removable actuator member that is fastened in removable manner on said body at said distal bearing surface, said removable actuator member having a radial dimension that is greater than the radial dimension of said bearing surface.

Advantageously, said reservoir contains a single dose of fluid.

In a variant, said reservoir contains only two doses of fluid.

Advantageously, said removable actuator member includes a hollow axial sleeve that is engaged in removable manner, in particular by friction, on said body, in particular around said distal bearing surface.

Advantageously, said removable actuator member includes a radial flange, such as a disk, that projects radially outwards relative to said distal bearing surface of said body.

Advantageously, said removable actuator member is made out of a flexible material, such as a thermoplastic elastomer (TPE).

Advantageously, blocking and/or pre-compression means are provided between said body and said dispenser head.

Advantageously, said blocking and/or pre-compression means comprise breakable bridges.

Advantageously, the area of said distal bearing surface is less than 100 square millimeters ($mm^2$), advantageously less than 80 $mm^2$, preferably about 60 $mm^2$.

Advantageously, the area of said removable actuator member is greater than 150 $mm^2$, advantageously greater than 220 $mm^2$, preferably about 515 $mm^2$.

These characteristics and advantages and others appear more clearly from the following detailed description, given by way of non-limiting example, and with reference to the accompanying drawing, in which.

Figure 3:
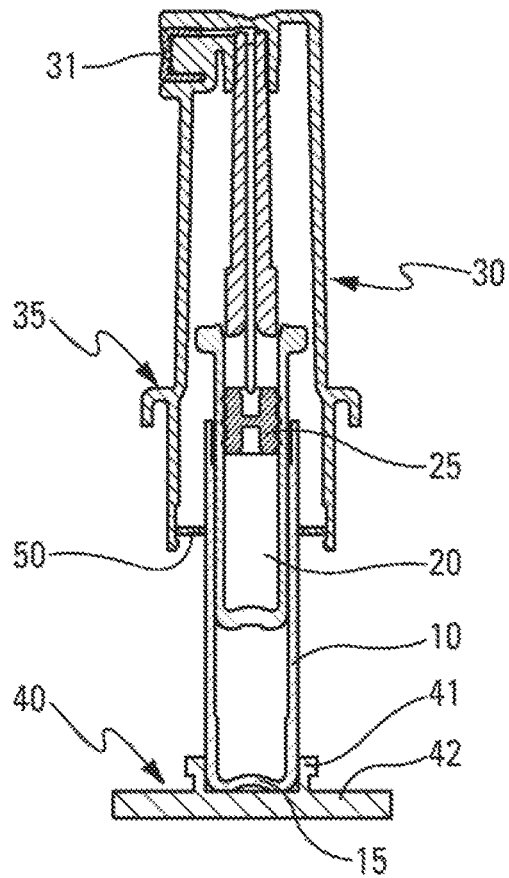
FIG. 3 is a diagrammatic section view of the FIG. 1 device, provided with the FIG. 2 removable actuator member, shown before actuation.
Figure 4:
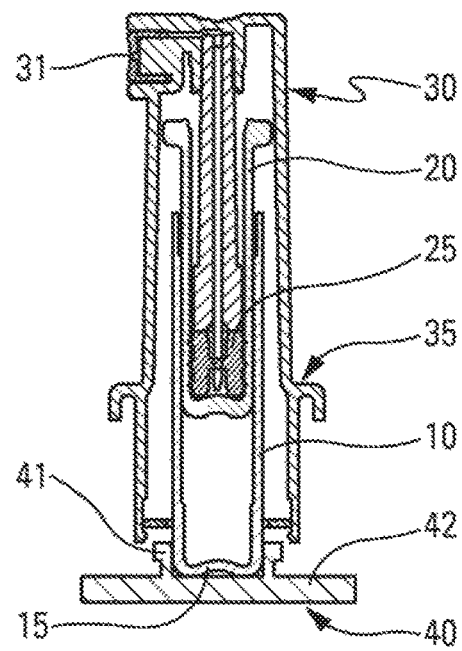
FIG. 4 is a view similar to the view in FIG. 3, shown after inhalation.

In the description, the terms "axial" and "radial" are relative to the longitudinal axis of the device shown in FIGS. 3 and 4. The terms "proximal" and "distal" are relative to the dispenser orifice.

The fluid dispenser device of the invention conventionally comprises a body 10 that supports, in stationary manner, a reservoir 20 containing fluid. A dispenser head 30 is assembled on said body 10 in axially movable manner relative to said reservoir 20, said dispenser head 30 being provided with a dispenser orifice 31.

In known manner, said dispenser head 30 includes a proximal bearing surface 35 that, during actuation, receives at least one, and typically two, of the user's fingers. Likewise, the body 10 includes a distal bearing surface 15 that, during actuation, is suitable for receiving one of the user's fingers, and typically the thumb.

A piston 25 is slidably mounted in the reservoir 20, said piston 25 being moved, during actuation, by the dispenser head 30 while said dispenser head is moving axially relative to the body 10 and thus relative to the reservoir 20.

In the invention, the device includes a removable actuator member 40 that co-operates in removable manner with said body 10 at said distal bearing surface 15. In particular, the removable actuator member 40 is fastened in removable manner on said body 10. The removable actuator member 40 has a radial dimension that is greater than the radial dimension of said bearing surface 15. Advantageously, the area of said distal bearing surface 15 is less than 100 $mm^2$, in particular less than 80 $mm^2$, in particular about 60 $mm^2$, whereas the area of said removable actuator member is advantageously greater than 150 mm², in particular greater than 220 mm², in particular about 515 mm². This thus increases the contact area between the user's thumb and the device during actuation, thereby making it easier to actuate the device by distributing the actuation force exerted by the thumb over a larger area of bearing surface. By making the actuation force more acceptable, the device of the invention also makes it easier to deliver an actuation stroke that is complete. This may be particularly advantageous for a large nominal dose, e.g. due to a long actuation stroke or to a viscous fluid.

Figure 1:
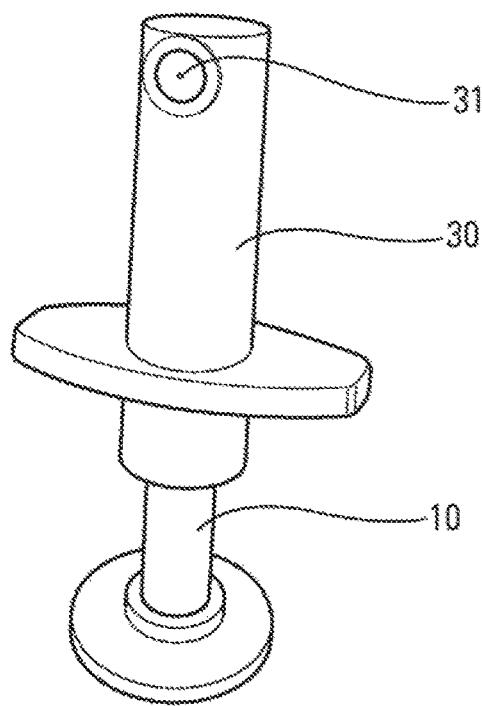
FIG. 1 is a diagrammatic perspective view of a dispenser device to which the invention applies.
Figure 2:
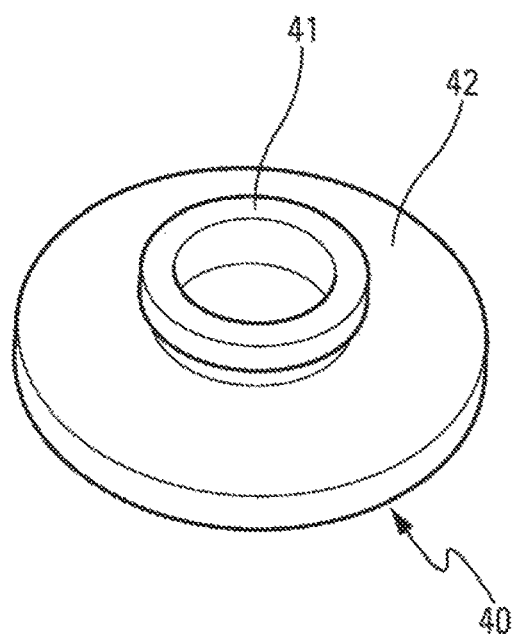
FIG. 2 is a perspective view of a detail of the removable actuator member, in an advantageous embodiment.

Advantageously, the removable actuator member 40 includes a hollow axial sleeve 41 that is engaged in removable manner, in particular by friction, on said body 10. As can be seen in FIGS. 1, 3, and 4, engagement preferably occurs around the distal bearing surface 15 of the body 10. Optionally, said hollow axial sleeve 41 may include clamping profiles, such as splines or the like, for promoting easy engagement and removal of said removable actuator member 40.

The removable actuator member 40 advantageously includes a radial flange 42, such as a disk, forming the substitute bearing surface that projects radially outwards relative to the distal bearing surface 15 of the body 10, thereby increasing the contact area with the thumb.

In order to avoid accidental actuation and to generate pre-compression in the user's hand during actuation, the device advantageously includes blocking and/or pre-compression means 50, preferably formed by breakable bridges arranged between the body 10 and the head 30. Naturally, other blocking and/or pre-compression means can be envisaged. Furthermore, the pre-compression means could be separate from the blocking means.

The addition of a removable actuator member 40 on the base of the body 10 makes the force to be provided by the user more acceptable as a result of the larger surface area in contact with the user's thumb.

Since said actuator member 40 is removable from the body, the user has the choice of whether to use it or not use it.

Said removable actuator member 40 is advantageously made out of a material that is relatively flexible, such as a TPE. This presents several advantages, including in particular:
 agreeable contact with the user's thumb; and
 simple assembly on the body 10 and equally simple retention by clamping.

Said removable actuator member 40 also presents the following advantages compared to a solution that is not removable from the body 10:
 the removable actuator member 40 can be removed easily after actuation, such that when the user pulls on it, it detaches from the body 10; it therefore cannot be used to dismantle the device, and thus gain access to the fluid remaining in the device after actuation;
 the flexibility of the material implies that said removable actuator member 40 becomes detached from the body 10 if the user does not push along the axis of the body; this makes it possible to avoid tilting, and thus limits the risks of a malfunction or of an incomplete dose.

The invention applies more particularly to devices of the single-dose or two-dose type, containing only a single dose or only two doses of fluid.

The present invention is described with reference to an advantageous implementation, however it should be understood that a person skilled in the art can apply any modification thereto without going beyond the ambit of the present invention as defined by the accompanying claims.

The invention claimed is:

1. A fluid dispenser device comprising a body that supports, in stationary manner, a reservoir containing fluid, a dispenser head assembled on said body so as to be axially movable relative to said reservoir, said dispenser head provided with a dispenser orifice, said dispenser head including a proximal bearing surface that, during actuation, for receiving at least one of a user's fingers, and said body including a distal bearing surface that, during actuation, is suitable for receiving another one of the user's fingers, said device comprising a removable actuator member that is fastened in removable manner on said body at said distal bearing surface so as to be detachable from the body by the user, said removable actuator member having a radial dimension that is greater than the radial dimension of said bearing surface; wherein the area of said distal bearing surface being less than 100 mm², the area of said removable actuator member is greater than 150 mm², and blocking or pre-compression means are provided between said body and said dispenser head.

2. A device according to claim 1, wherein said reservoir contains a single dose of fluid.

3. A device according to claim 1, wherein said reservoir contains only two doses of fluid.

4. A device according to claim 1, wherein said removable actuator member includes a hollow axial sleeve that is engaged in removable manner on said body.

5. A device according to claim 1, wherein said removable actuator member includes a radial flange that projects radially outwards relative to said distal bearing surface of said body.

6. A device according to claim 1, wherein said removable actuator member is made out of a flexible material.

7. A device according to claim 1, wherein said blocking and/or pre-compression means comprise breakable bridges.

8. The device according to claim 1, wherein the area of said distal bearing surface being less than 80 mm².

9. The device according to claim 1, wherein the area of said distal bearing surface being about 60 mm².

10. The device according to claim 1, wherein and the area of said removable actuator member is greater than 220 mm².

11. The device according to claim 1, wherein and the area of said removable actuator member is about 515 mm².

12. The device according to claim 1, wherein the proximal bearing surface is configured to receive two of the user's fingers during actuation and the distal bearing surface is configured to receive the user's thumb during actuation.

13. The device according to claim 1, wherein said removable actuator member includes a hollow axial sleeve that is removably engaged by friction on said body around said distal bearing surface.

14. A fluid dispenser device comprising:
 a body that supports and is directly attached to a reservoir containing fluid;
 a dispenser head assembled on the body so as to be axially movable relative to the reservoir, wherein the dispenser head is provided with a dispenser orifice and a bearing surface, the bearing surface configured to engage with one or two fingers of a user of the fluid dispenser during actuation; and
 a removable actuator member directly fastened in removable manner to the body at a distal end of the body furthest from the dispenser orifice, the removable actuator member has a pressing surface with a surface area configured to engage with a thumb of the user during actuation, the surface area of the pressing surface is greater than a surface area of the distal end of the body; and wherein the surface area of the distal end of the body is less than 100 mm², the surface area of the pressing surface is greater than 150 mm², and blocking or pre-compression means are provided between the body and the dispenser head.

15. The device according to claim 14, wherein the body is disposed between the reservoir and the removable actuator member.

16. A device according to claim 1, wherein said removable actuator member includes a radial flange in the form of a disk that projects radially outwards relative to said distal bearing surface of said body.

17. A device according to claim 1, wherein said removable actuator member is made out of TPE flexible material.

* * * * *